United States Patent
Okamura

(10) Patent No.: US 11,771,409 B2
(45) Date of Patent: Oct. 3, 2023

(54) TREATMENT METHOD

(71) Applicant: TERUMO KABUSHIKI KAISHA, Tokyo (JP)

(72) Inventor: Ryo Okamura, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 380 days.

(21) Appl. No.: 16/880,176

(22) Filed: May 21, 2020

(65) Prior Publication Data

US 2020/0281577 A1 Sep. 10, 2020

Related U.S. Application Data

(63) Continuation of application No. 15/938,173, filed on Mar. 28, 2018, now Pat. No. 10,687,796.

(30) Foreign Application Priority Data

Mar. 29, 2017 (JP) .................................. 2017-066144

(51) Int. Cl.
| | | |
|---|---|---|
| A61B 17/00 | (2006.01) | |
| A61B 17/132 | (2006.01) | |
| A61F 13/36 | (2006.01) | |
| A61B 17/135 | (2006.01) | |

(52) U.S. Cl.
CPC ........ *A61B 17/0057* (2013.01); *A61B 17/132* (2013.01); *A61B 17/135* (2013.01); *A61F 13/36* (2013.01); *A61B 17/1325* (2013.01); *A61B 2017/00557* (2013.01); *A61B 2017/00654* (2013.01); *A61B 2017/00659* (2013.01); *A61B 2017/00862* (2013.01); *A61B 2017/00951* (2013.01)

(58) Field of Classification Search
CPC . A61B 17/132; A61B 17/135; A61B 17/1325; A61B 2017/00557; A61B 2017/00862; A61F 13/36
See application file for complete search history.

(56) References Cited

U.S. PATENT DOCUMENTS

| | | | | |
|---|---|---|---|---|
| 2011/0040258 | A1* | 2/2011 | Robison | A61M 25/02 604/179 |
| 2013/0079695 | A1* | 3/2013 | Huey | A61L 15/28 602/49 |

FOREIGN PATENT DOCUMENTS

| | | | | |
|---|---|---|---|---|
| JP | 2008119517 A | * | 5/2008 | ......... A61B 17/1325 |
| JP | 2008119517 A | | 5/2008 | |

OTHER PUBLICATIONS

Mangin, Lionel, "The Transulnar Approach for Coronary Intervention", vol. 17, Issue 2, pp. 77-79.

* cited by examiner

*Primary Examiner* — Bhisma Mehta
*Assistant Examiner* — Rachel T. Smith
(74) *Attorney, Agent, or Firm* — BUCHANAN INGERSOLL & ROONEY PC

(57) ABSTRACT

A hemostatic device is disclosed, which includes a covering portion disposed so as to cover a site where bleeding is to be stopped on a hand of a patient; a pressing portion that compresses the site where bleeding is to be stopped when the covering portion covers the site where bleeding is to be stopped; a band portion wrappable around a periphery of the patient's hand at the site where bleeding is to stopped; a restriction portion that restricts movement of the securing portion in an axial direction; and wherein the pressing portion is not disposed on the centerline of the restriction.

20 Claims, 10 Drawing Sheets

TREATMENT METHOD

CROSS-REFERENCES TO RELATED APPLICATIONS

This application is a continuation of U.S. application Ser. No. 15/938,173, filed on Mar. 28, 2018, which claims priority to Japanese Application No. 2017-066144 filed on Mar. 29, 2017, the entire contents of which are incorporated herein by reference.

TECHNICAL FIELD

The present disclosure generally relates to a treatment method of introducing a medical elongated body into a palmar artery of a patient.

BACKGROUND DISCUSSION

In the related art, a medical procedure is known in which various medical elongated bodies (for example, a sheath tube of an introducer) are introduced into a blood vessel via a puncture site formed in the blood vessel of an arm of a patient so as to treat a lesion site. In a case where this medical procedure is performed, an operator performs hemostasis on the puncture site when removing the medical elongated body from the puncture site (See Japanese Patent Application Publication No. 2008-119517).

A radial artery or an ulnar artery extending in an arm of a human body is connected to a palmar artery which bypasses a hand side. Therefore, for example, the operator forms the puncture site in the palmar artery, thereby enabling the medical elongated body to be inserted into the radial artery on an arm side. In addition, if the puncture site is formed in the hand instead of the arm or a wrist, the patient can move the arm or the wrist while the hemostasis is performed (i.e., while a compressive force is applied to the puncture site). Accordingly, various body motions are more freely available, thereby improving quality of life (QOL).

In a case where the puncture site is formed in the hand as described above, for example, the operator can puncture the radial artery side (side close to the radial artery) of the palmar artery. However, the radial artery side of the palmar artery extends so as to bypass a periphery of a thumb's bone along a thickness direction of the hand. Accordingly, the blood vessel is bent. Therefore, if the operator forms the puncture site on the radial artery side of the palmar artery and introduces the medical elongated body through the radial artery side of the palmar artery, the medical elongated body may kink, or alternatively, torque transmission ability and operability of the medical elongated body (or a medical device introduced into a living body via the medical elongated body) may become poor. In this case, the operator cannot smoothly realize the medical procedure, which leads to an increase in the burden on the patient.

SUMMARY

A treatment method is disclosed, which is capable of suppressing kink, poor torque transmission ability, and poor operability of a medical elongated body inserted into a blood vessel.

In accordance with an exemplary embodiment, a treatment method is disclosed, which includes causing a medical elongated body introduced into a blood vessel via a puncture site formed on an ulnar artery side of a palmar artery of a patient, to indwell the puncture site.

According to the above-described treatment method, the medical elongated body is located on the ulnar artery side of the palmar artery which has relatively less bending of the blood vessel. Therefore, an operator can cause the medical elongated body to indwell the inside of the palmar artery of the patient, while suppressing kink, poor torque transmission ability, and poor operability of the medical elongated body.

A treatment method is disclosed, the treatment method comprising: delivering a medical device to a lesion site of a blood vessel through a puncture site formed on an ulnar artery side of a palmar artery of a patient; removing the medical device from the blood vessel through the ulnar artery and the palmar artery, after treatment is performed on the lesion site using the medical device; locating a hemostatic device around a hemostatic target site present in a hand of the patient; providing the hemostatic device with a covering portion which covers the hemostatic target site, and a pressing portion which presses the hemostatic target site in a state where the covering portion covers the hemostatic target site; locating the pressing portion at the hemostatic target site so that the pressing portion overlaps the puncture site; and fixing the covering portion to the hand so that the pressing portion presses the puncture site.

A treatment method is disclosed, the treatment method comprising: removing a medical device from a blood vessel through a puncture site formed on an ulnar artery side of a palmar artery of a patient; locating a hemostatic device around a hemostatic target site present in a hand of the patient; providing the hemostatic device with a covering portion which covers the hemostatic target site, and a pressing portion which presses the hemostatic target site in a state where the covering portion covers the hemostatic target site; locating the pressing portion at the hemostatic target site so that the pressing portion overlaps the puncture site; fixing the covering portion to the hand so that the pressing portion presses the puncture site; providing the covering portion with a fixing portion which surrounds at least a portion of the hand while covering the pressing portion, and a restriction portion which restricts movement of the fixing portion in an axial direction; and locating the restriction portion between adjacent fingers of the hand, in a state where the covering portion is fixed to the hand so that the pressing portion presses the puncture site.

In accordance with an aspect, a hemostatic device is disclosed comprising: a covering portion disposed so as to cover a site where bleeding is to be stopped on a hand of a patient; a pressing portion that compresses the site where bleeding is to be stopped when the covering portion covers the site where bleeding is to be stopped; a band portion wrappable around a periphery of the patient's hand at the site where bleeding is to be stopped, the pressing portion being mounted on the band portion at a position between free ends of the band portion, the pressing portion being located closer to one of the free ends of the band portion than an other of the free ends of the band portion, the band portion including a securing portion that secures the band portion in a state in which the band portion is wrapped around the periphery of the hand of the patient at the site where bleeding is to be stopped; a restriction portion that restricts movement of the securing portion in an axial direction, the restriction portion including a first end portion secured to the band portion, a second end portion that is attachable to and detachable from the band portion and an intermediate portion located between the first end portion and the second end portion, the restriction portion being positionable between adjacent fingers of the hand of the patient and possessing a centerline extending parallel to an extending direction of the intermediate portion and extending through a center of a width of the intermediate portion; and wherein the pressing portion is not disposed on the centerline of the restriction.

In accordance with another aspect, a hemostatic device is disclosed comprising: a covering portion disposed so as to cover a site where bleeding is to be stopped on a hand of a patient; a pressing portion that compresses the site where bleeding is to be stopped when the covering portion covers the site where bleeding is to be stopped; a band portion wrappable around a periphery of the patient's hand at the site where bleeding is to stopped, the pressing portion being mounted on the band portion at a position between free ends of the band portion, the pressing portion being located closer to one of the free ends of the band portion than an other of the free ends of the band portion, the band portion including a securing portion that secures the band portion in a state in which the band portion is wrapped around the periphery of the hand of the patient at the site where bleeding is to be stopped; a restriction portion that restricts movement of the securing portion in an axial direction, the restriction portion including a first end portion secured to the band portion and a second end portion that is attachable to and detachable from the band portion, the restriction portion being positionable between adjacent fingers of the hand of the patient; and the hemostatic device being configured so that in a state in which the second end portion of the restriction portion is attached with the band portion while the band portion is wrapped around the periphery of the patient's hand at the site where the bleeding is to be stopped, the pressing portion is not disposed on a centerline of the restriction portion extending from the first end portion secured to the band portion towards a position of the restriction portion between the adjacent fingers of the hand of the patient.

In accordance with an aspect, a hemostatic device is disclosed comprising: a covering portion configured to cover a site where bleeding is to be stopped on a hand of a patient; an expandable pressing portion that is expandable to apply a compressive force to the site where bleeding is to be stopped when the covering portion covers the site where bleeding is to be stopped, the expandable pressing portion possessing a center portion located at a center position in a plane direction of the expandable pressing portion; the covering portion including: a first band part that extends away from the pressing portion in a first direction, the first band part including one end fixed relative to the pressing portion and an opposite free end, the first band part including a first fastener, the free end of the first band part being spaced from a center of the expandable pressing portion by a first distance; a second band part that extends away from the pressing portion in a second direction, the second direction being different from the first direction, the second band part including one end fixed relative to the pressing portion and an opposite free end, the second band part including a second fastener, the free end of the second band part being spaced from a center of the expandable pressing portion by a second distance, the second distance being greater than the first distance; the first band part and the second band part possessing respective lengths that allow the first band part and the second band part to be wrapped around a periphery of the patient's hand while the expandable pressing portion overlies the site where bleeding is to be stopped and that allow the first and second fasteners to detachably engage one another to hold the expandable pressing portion on the patient's hand at the site where bleeding is to be stopped; a third band part including one end fixed relative to the pressing portion and an opposite free end, the third band part extending in a third direction different from the first and second directions, the third band part including a third fastener, the third band part also including an intermediate portion located between the one end and the opposite free end of the third band, the third band part possessing a centerline extending parallel to the third direction and extending through a center of a width of the intermediate portion; the third band part possessing a length allowing the intermediate portion of the third band part to be positioned between two fingers of the hand of the patient and allowing the third fastener to be detachably engage the first fastener of the first band part or the second fastener of the second band part to restrict movement of the expandable pressing portion in an axial direction; and the centerline of the third band part is offset to the center portion of the expandable pressing portion.

In accordance with another aspect, a hemostatic device is disclosed comprising: a covering portion disposed so as to cover a site where bleeding is to be stopped on a hand of a patient; a pressing portion that compresses the site where bleeding is to be stopped when the covering portion covers the site where bleeding is to be stopped, the pressing portion comprising a marker portion for aligning the pressing portion with the site where bleeding is to be stopped so that the pressing portion overlies the site where bleeding is to be stopped; a band portion wrappable around a periphery of the patient's hand at the site where bleeding is to stopped, the pressing portion being mounted on the band portion at a position between free ends of the band portion, the pressing portion being located closer to one of the free ends of the band portion than an other of the free ends of the band portion, the band portion including a holding portion that secures the band portion in a state in which the band portion is wrapped around the periphery of the hand of the patient at the site where bleeding is to be stopped; a restriction portion that restricts movement of the holding portion in an axial direction, the restriction portion including a first end portion secured to the band portion and a second end portion that is attachable to and detachable from the band portion, the restriction portion being positionable between adjacent fingers of the hand of the patient; and the hemostatic device being configured so that in a state in which the second end portion of the restriction portion is attached with the band portion while the band portion is wrapped around the periphery of the patient's hand at the site where the bleeding is to be stopped, the marker portion is offset on a centerline of the restriction portion extending from the first end portion secured to the band portion towards a position of the restriction portion between the adjacent fingers of the hand of the patient.

BRIEF DESCRIPTION OF THE DRAWINGS

FIGS. 3A and 3B are perspective views illustrating the state where the hemostatic device according to the first embodiment is mounted on the hand of the patient, and wherein FIG. 3A is a perspective view when viewed from a dorsal side of the hand of the patient, and FIG. 3B is a perspective view when viewed from a palm side.

DESCRIPTION OF EMBODIMENTS

Figure 1:
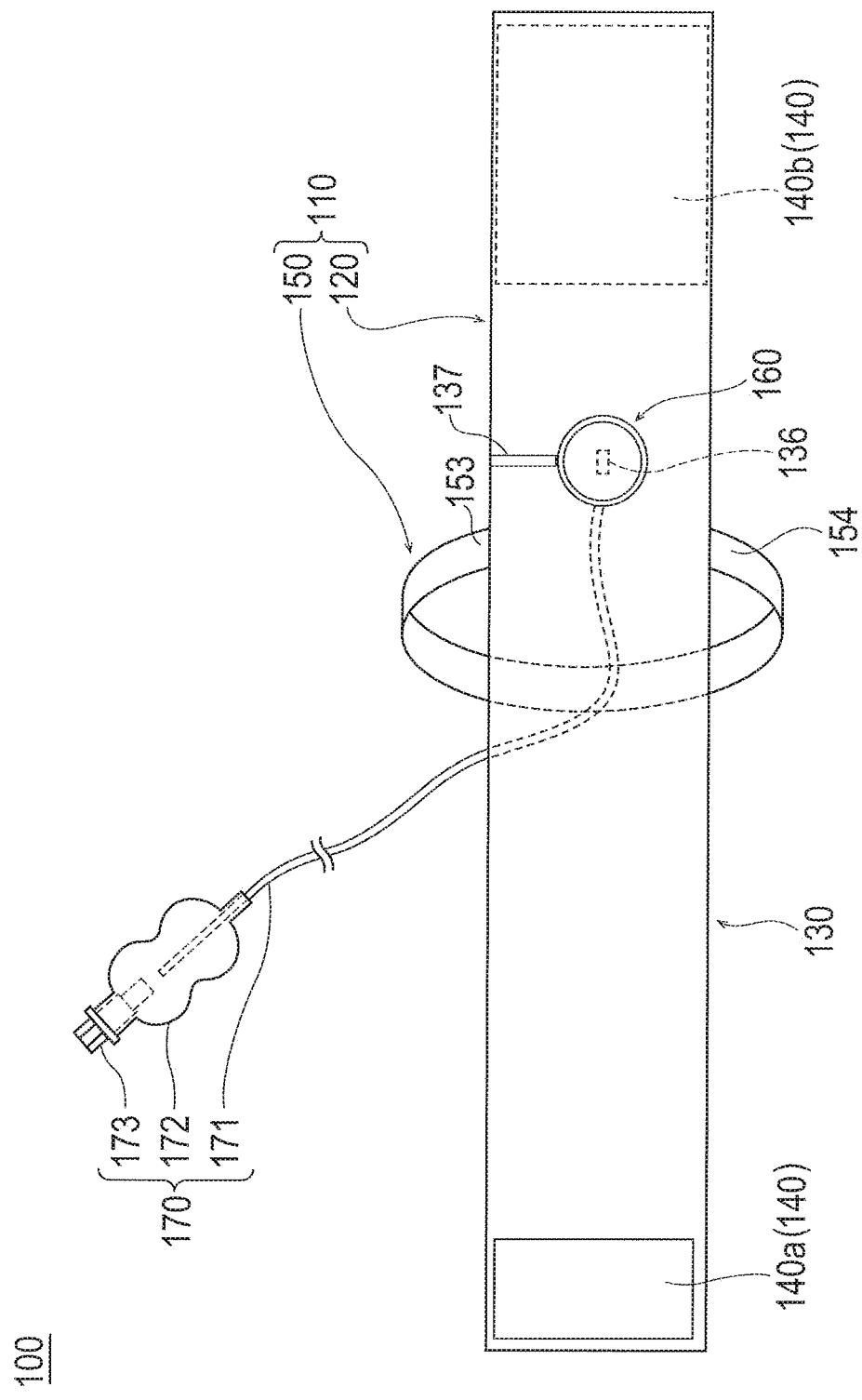
FIG. 1 is a plan view when a hemostatic device according to a first embodiment of the present disclosure is viewed from an inner surface side.

Hereinafter, embodiments according to the present disclosure will be described with reference to the accompanying drawings. Note that, the following description does not limit the technical scope or definition of terms described in appended claims. In addition, dimensional ratios in the drawings are exaggerated for convenience of description, and may differ from actual ratios in some cases.

In accordance with an exemplary embodiment, a treatment method and a hemostatic device 100 according to a first embodiment will be described with reference to FIGS. 1 to 10. FIGS. 1 to 5 are views for describing a device configuration of the hemostatic device 100. FIG. 6 is a view for describing each blood vessel in a hand H of a patient. FIGS. 7 to 10 are views for describing the treatment method and a use procedure of the hemostatic device according to the first embodiment.

Figure 7:
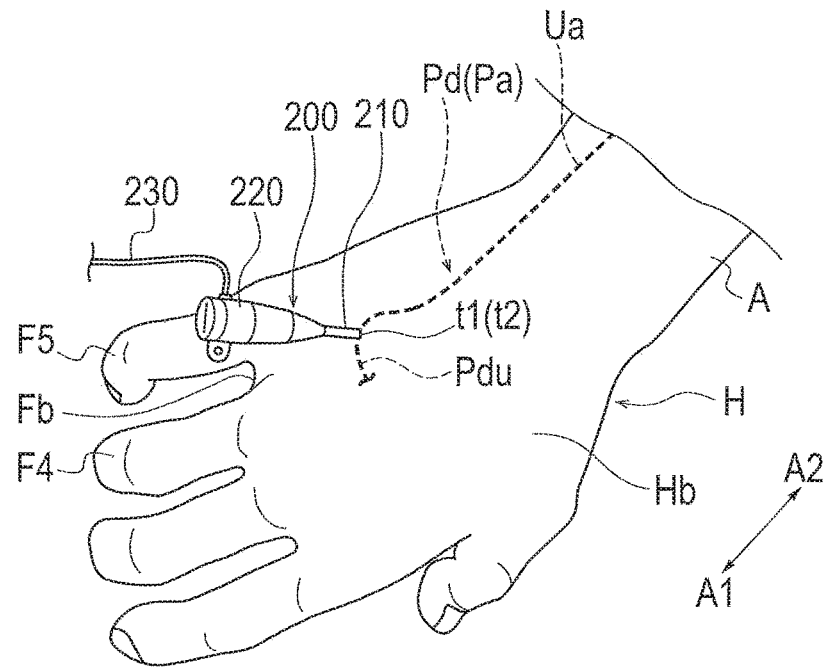
FIG. 7 is a perspective view for describing a treatment method and a use procedure of the hemostatic device according to the first embodiment.
Figure 8:
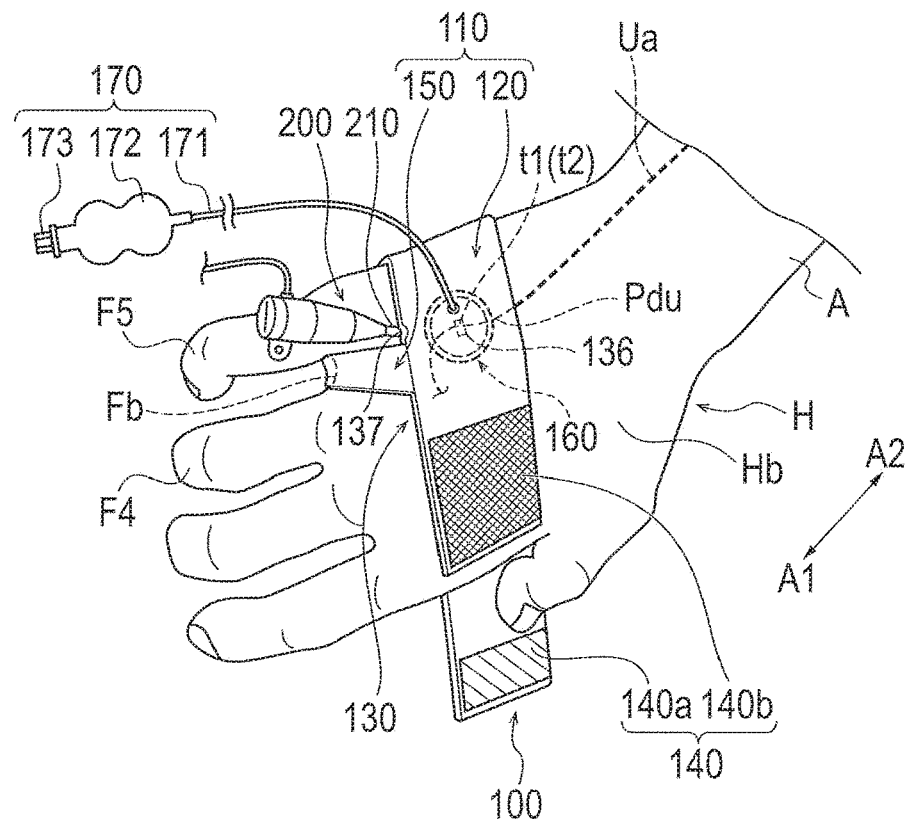
FIG. 8 is a perspective view for describing a treatment method and a use procedure of the hemostatic device according to the first embodiment.
Figure 9:
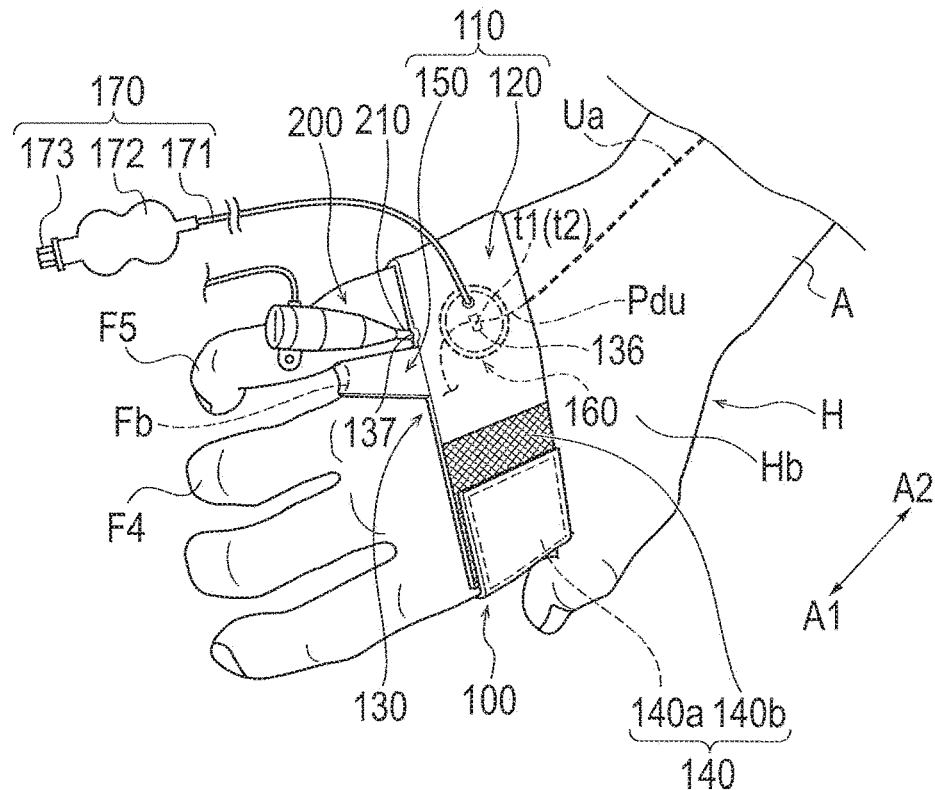
FIG. 9 is a perspective view for describing a treatment method and a use procedure of the hemostatic device according to the first embodiment.
Figure 10:
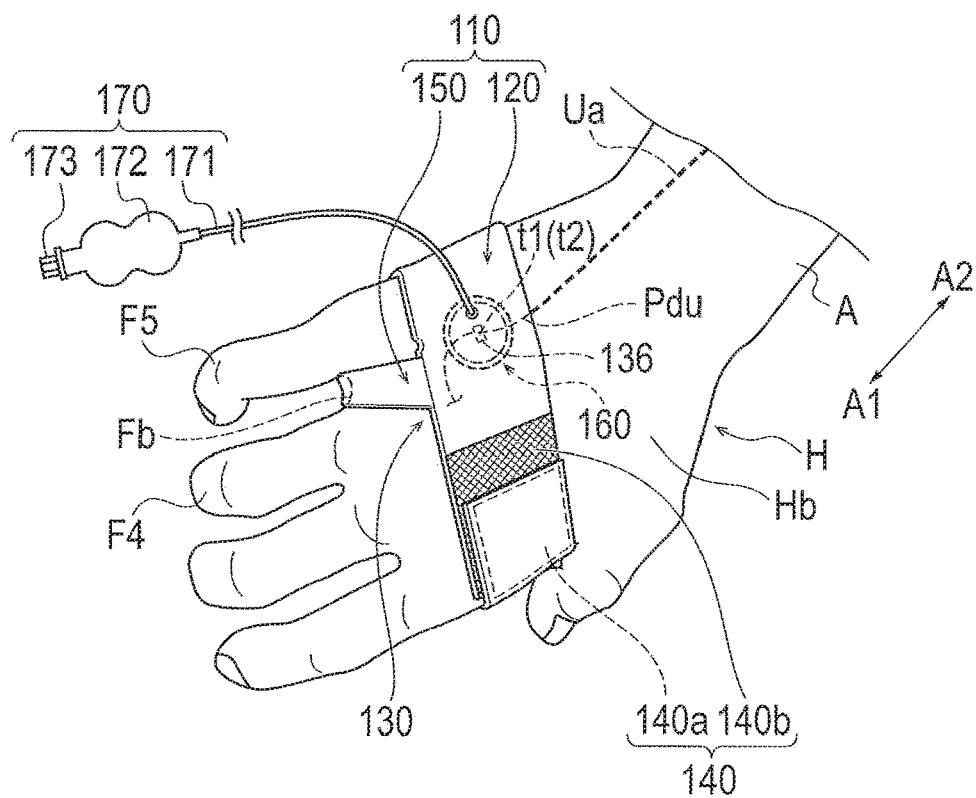
FIG. 10 is a perspective view for describing a treatment method and a use procedure of the hemostatic device according to the first embodiment.

As illustrated in FIG. 7, in the treatment method according to the present embodiment, a sheath tube 210 (corresponding to a "catheter") of an introducer 200 is caused to indwell a puncture site t2 formed in an ulnar artery side Pdu of a palmar artery Pa (deep palmar artery Pd) in a hand H of a patient. In addition, as illustrated in FIGS. 8 to 10, the hemostatic device 100 according to the present embodiment is used for performing hemostasis on the puncture site t2 after the sheath tube 210 of the introducer 200 is removed from the puncture site t2 formed on the ulnar artery side Pdu of the palmar artery Pa.

Prior to description of the treatment method and the hemostatic device 100 according to the present embodiment, the hand H of the patient and each vessel in the hand H will be described with reference to FIG. 6. FIG. 6 schematically illustrates a plan view when the hand (right hand) H of the patient is viewed from a dorsal Hb side of the hand of the patient.

A radial artery Ra and an ulnar artery Ua which are branched from a brachial artery near an elbow extend in an arm A of the patient. The radial artery Ra and the ulnar artery Ua are connected to each other in an arc shape (arcuate shape) in the hand H, thereby forming the palmar artery (palmar arterial arch) Pa. In addition, the palmar artery Pa includes the deep palmar artery (deep palmar artery arch) Pd formed by a deep palmar branch where the radial artery Ra and the ulnar artery Ua are branched on the dorsal Hb side of the hand, and a superficial palmar artery (superficial palmar arterial arch) Pf formed by a superficial palmar branch where the radial artery Ra and the ulnar artery Ua are branched on a palm Hp side.

In the present embodiment, a virtual line C dividing the palmar artery Pa at a substantially central position in a width direction (lateral direction in FIG. 6) of the hand H is set as a boundary. A portion (region) extending to the radial artery Ra side in the deep palmar artery Pd included in the palmar artery Pa can be defined as a radial artery side Pdr of the deep palmar artery Pd. A portion (region) extending to the ulnar artery Ua side in the deep palmar artery Pd included in the palmar artery Pa can be defined as an ulnar artery side Pdu (hereinafter, also referred to as the "ulnar artery side Pdu of the palmar artery Pa") of the deep palmar artery Pd.

In addition, when the virtual line C illustrated in FIG. 6 is set as the boundary, a portion (region) extending to the radial artery Ra side in the superficial palmar artery Pf included in the palmar artery Pa can be defined as a radial artery side Pfr of the superficial palmar artery Pf. A portion (region) extending to the ulnar artery Ua side in the superficial palmar artery Pf included in the palmar artery Pa can be defined as an ulnar artery side Pfu of the superficial palmar artery Pf.

An inter-finger portion (inter-finger paddle) Fb is present in adjacent fingers F1 to F5 (a thumb F1, an index finger F2, a middle finger F3, a ring finger F4, and a little finger F5). A fingertip direction of each of the fingers F1 to F5 is indicated by an arrow A1, and a direction from a wrist W toward an elbow side is indicated by an arrow A2. In the description herein, a direction indicated by the arrows A1-A2 is set as an "axial direction".

In the present embodiment, the hand H is defined as a portion including the dorsal Hb side of the hand and the palm Hp which are located on the fingertip side farther from the wrist (joint connecting the palm and the arm) W. Note that, in FIG. 6, a boundary portion between the wrist W and the hand H is illustrated using a virtual line B.

Figure 4:
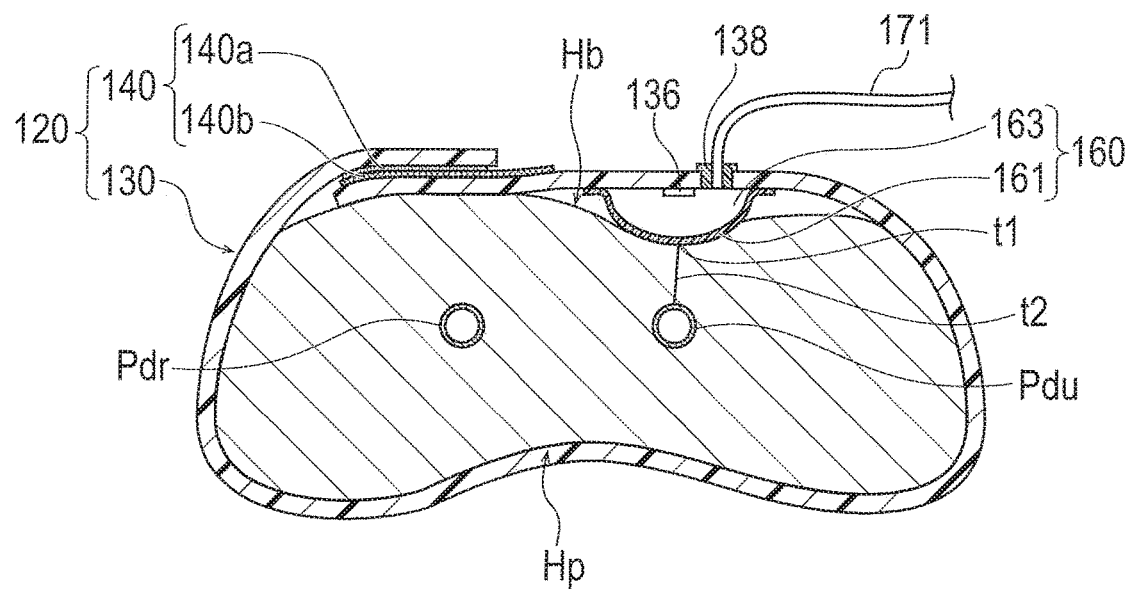
FIG. 4 is a cross-sectional view (horizontal cross-sectional view of the hand) taken along line IV-IV illustrated in FIG. 3A.

As illustrated in FIG. 4, in the present embodiment, a "hemostatic target site t1" means a perforation and a peripheral portion of the perforation which are formed in a skin surface layer of a patient by a medical instrument such as a puncture needle. A "puncture site t2" means a subcutaneous portion (including a blood vessel) of a living body in which a perforation is formed by a medical instrument such as a puncture needle.

In addition, in the present embodiment, the puncture site t2 is formed on the ulnar artery side Pdu of the palmar artery Pa (refer to FIGS. 4 and 6). More specifically, for example, in a state where the hand H of the patient is spread as illustrated in FIG. 6, the puncture site t2 is formed between a center line c1 of the ring finger F4 on the dorsal Hb side of the hand and a center line c2 of the root of the little finger F5 (position where the center line c1 and the center line c2 intersect each other or a peripheral portion of the intersection of the center line c1 and the center line c2).

Next, the hemostatic device 100 will be described.

As illustrated in FIGS. 1 to 3B, the hemostatic device 100 has a covering portion 110 located so as to cover the hemostatic target site t1 of the hand H of the patient, and a pressing portion 160 which presses the hemostatic target site t1 in a state where the covering portion 110 covers the hemostatic target site t1.

Figure 2:
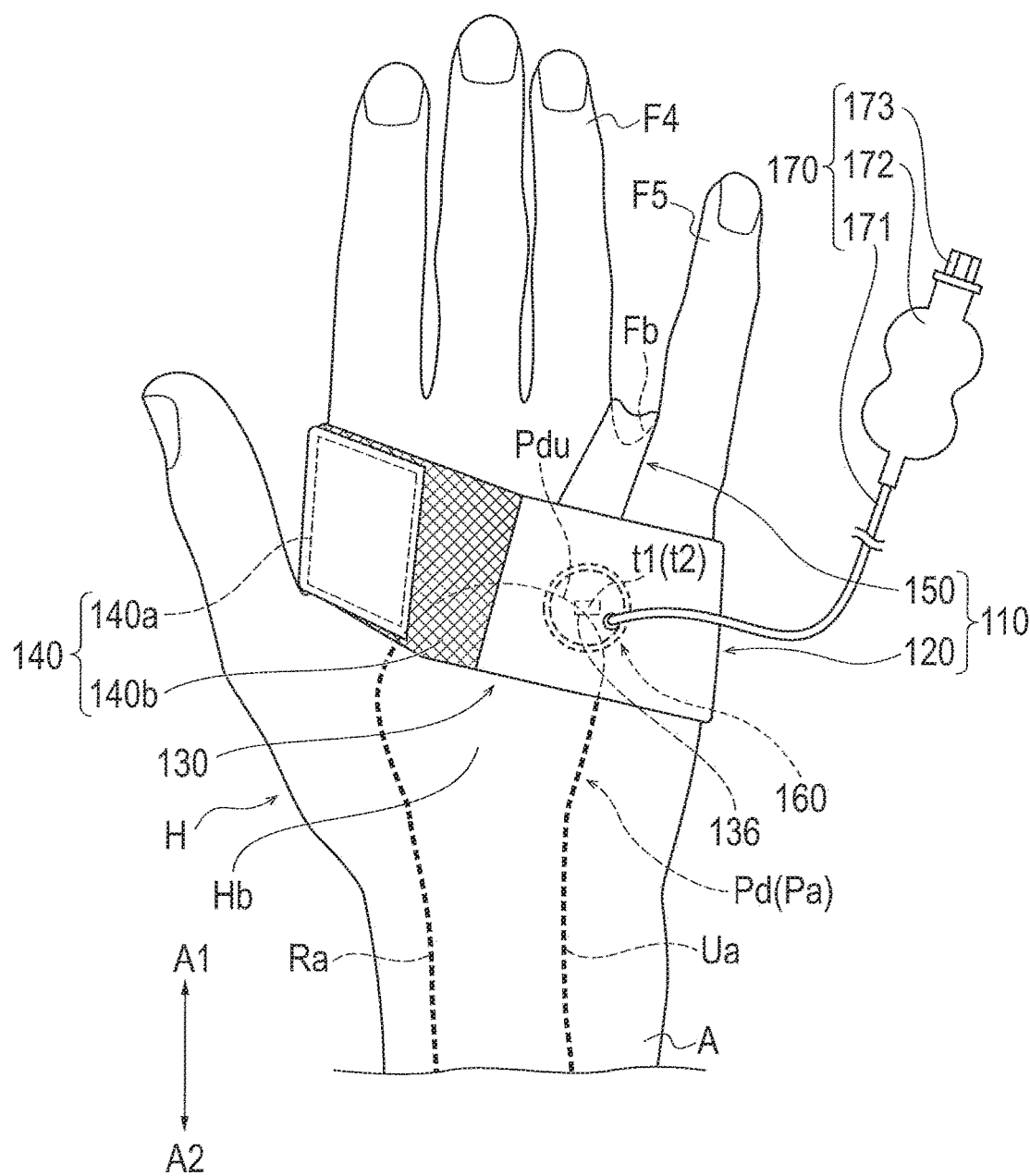
FIG. 2 is a plan view illustrating a state where the hemostatic device according to the first embodiment is mounted on a hand of a patient.

As illustrated in FIGS. 1 and 2, in accordance with an exemplary embodiment, the covering portion 110 has a fixing portion 120 which surrounds at least a portion of the hand H while covering the pressing portion 160, and a restriction portion 150 which restricts the movement of the fixing portion 120 in the axial direction.

Figure 3A:
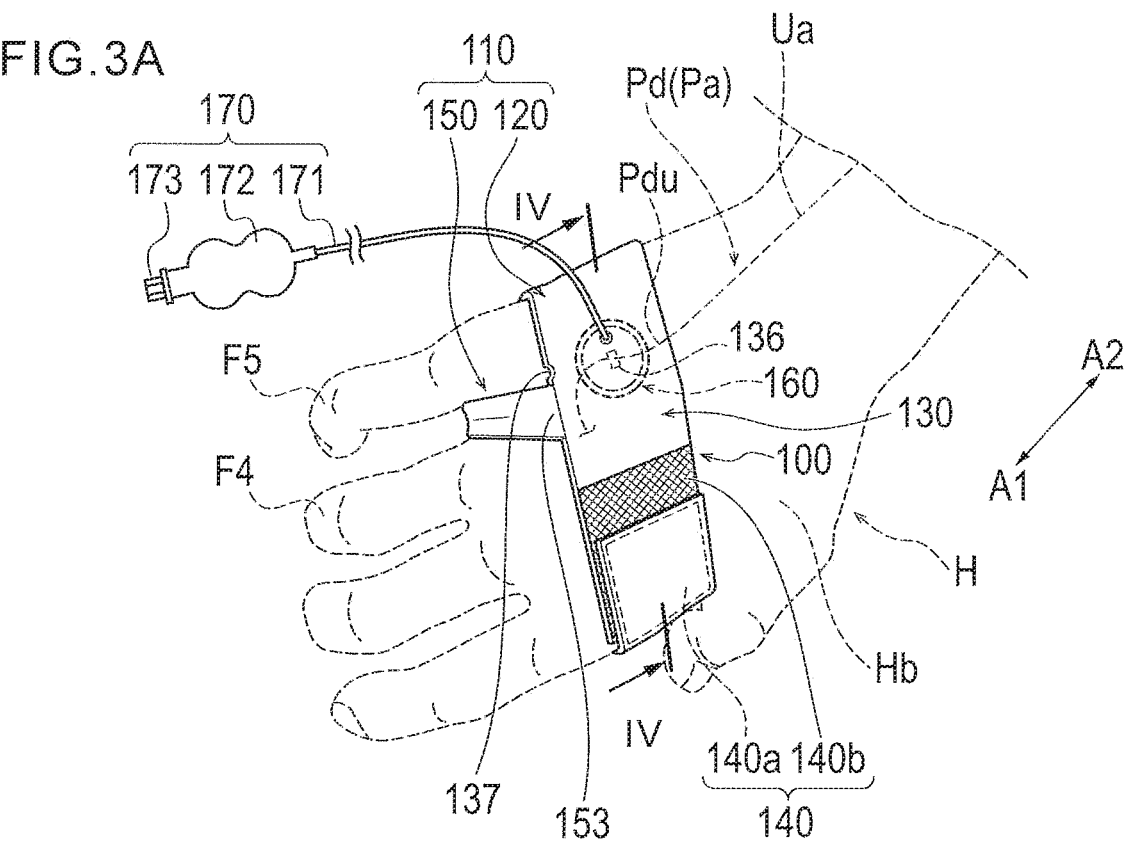
Figure 3B:
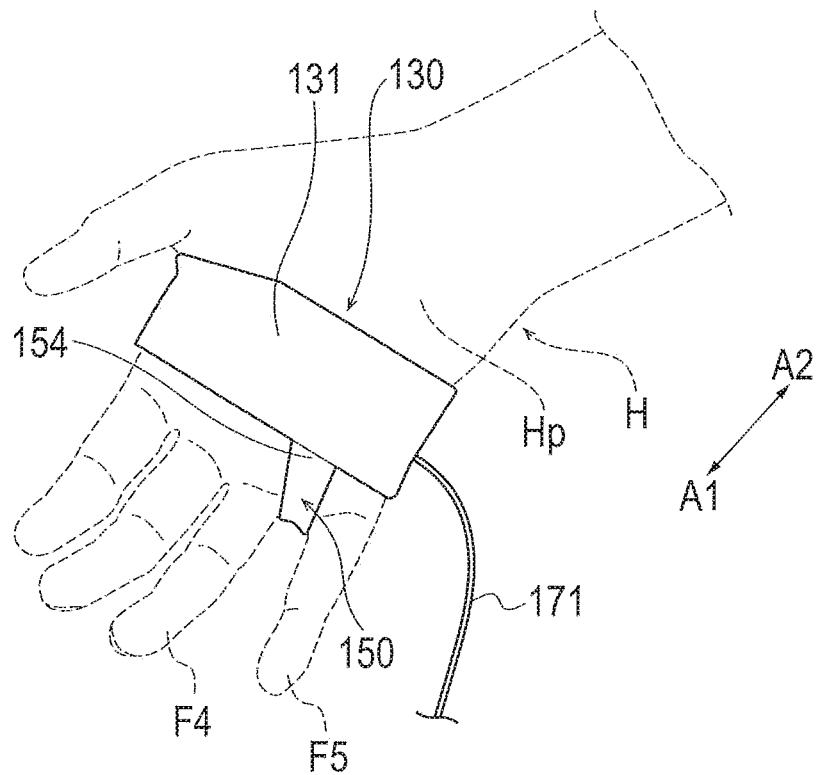

As illustrated in FIGS. 1, 3A, and 3B, the fixing portion 120 includes a band portion 130 wrapped around the hemostatic target site t1 of the hand H, and a holding portion 140 which fixes the band portion 130 in a state where the band portion 130 is wrapped around the hand H.

As illustrated in FIG. 1, the band portion 130 is configured to serve as a flexible band-like member. In the description herein, when the band portion 130 is wrapped around the hand H, a surface (mounting surface) where the band portion faces a body surface of the hand H is referred to as an "inner surface", and a surface opposite thereto is referred to as an "outer surface". Note that, FIG. 1 illustrates a plan view of the hemostatic device 100 when viewed from the inner surface side of the band portion 130.

As illustrated in FIGS. 3A, 3B, and 4, the band portion 130 is wound substantially once around an outer periphery of the hand H.

In the band portion 130, a male side (or female side) 140a of a hook and loop fastener, which is generally called a magic tape (registered trademark), is located on an inner surface side of a portion near the left end in FIG. 1. In addition, in the band portion 130, a female side (or male side) 140b of the hook and loop fastener is located on an outer surface side of a portion near the right end in FIG. 1.

The male side 140a of the hook and loop fastener of the band portion 130 and the female side 140b of the hook and loop fastener of the band portion 130 configure the holding portion 140. As illustrated in FIGS. 2 and 4, an operator or the like wraps the band portion 130 around the hand H, and joins the male side 140a of the hook and loop fastener and the female side 140b of the hook and loop fastener to each other. In this manner, the operator can fix the band portion 130 to the hand H of the patient.

Note that, the holding portion 140 is not particularly limited as long as the holding portion 140 has a configuration capable of fixing the band portion 130 in a state where the band portion 130 is wound around the hand H. For example, a snap, a button, a clip, or a frame member through which an end portion of the band portion 130 passes may be used.

The material from which the band portion 130 is made is not particularly limited as long as the material is flexible. For example, the material can include polyolefin such as polyvinyl chloride, polyethylene, polypropylene, polybutadiene, and ethylene-vinyl acetate copolymer (EVA), polyester such as polyethylene terephthalate (PET) and polybutylene terephthalate (PBT), various thermoplastic elastomers such as polyvinylidene chloride, silicone, polyurethane, polyamide elastomer, polyurethane elastomer, and polyester elastomer, nylon, nylon elastomer, or any desired combination of the materials (e.g., a blend resin, polymer alloy, or a layered product).

In addition, it can be preferable that a portion overlapping at least the pressing portion 160 in the band portion 130 is substantially transparent. However, the above-described portion of the band portion 130 is not limited to the transparent portion, and may be translucent or colored transparent. Since the band portion 130 is formed in this way, when the hemostatic device 100 is mounted on the hand H of the patient (refer to FIG. 8), the operator can view and recognize the hemostatic target site t1 from the outer surface side of the band portion 130. Therefore, the operator can easily align a marker portion 136 (to be described later) with the hemostatic target site t1.

Figure 5:
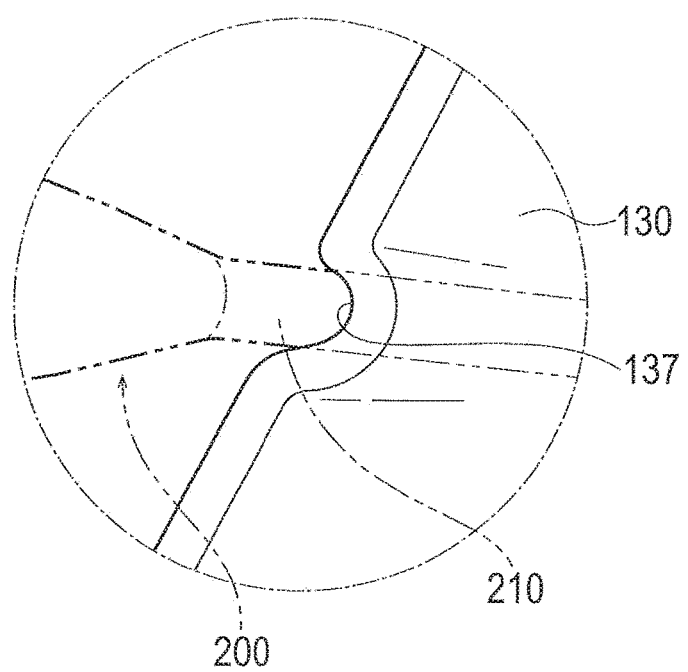
FIG. 5 is a perspective view illustrating an enlarged indwelling portion of the hemostatic device according to the first embodiment.
Figure 6:
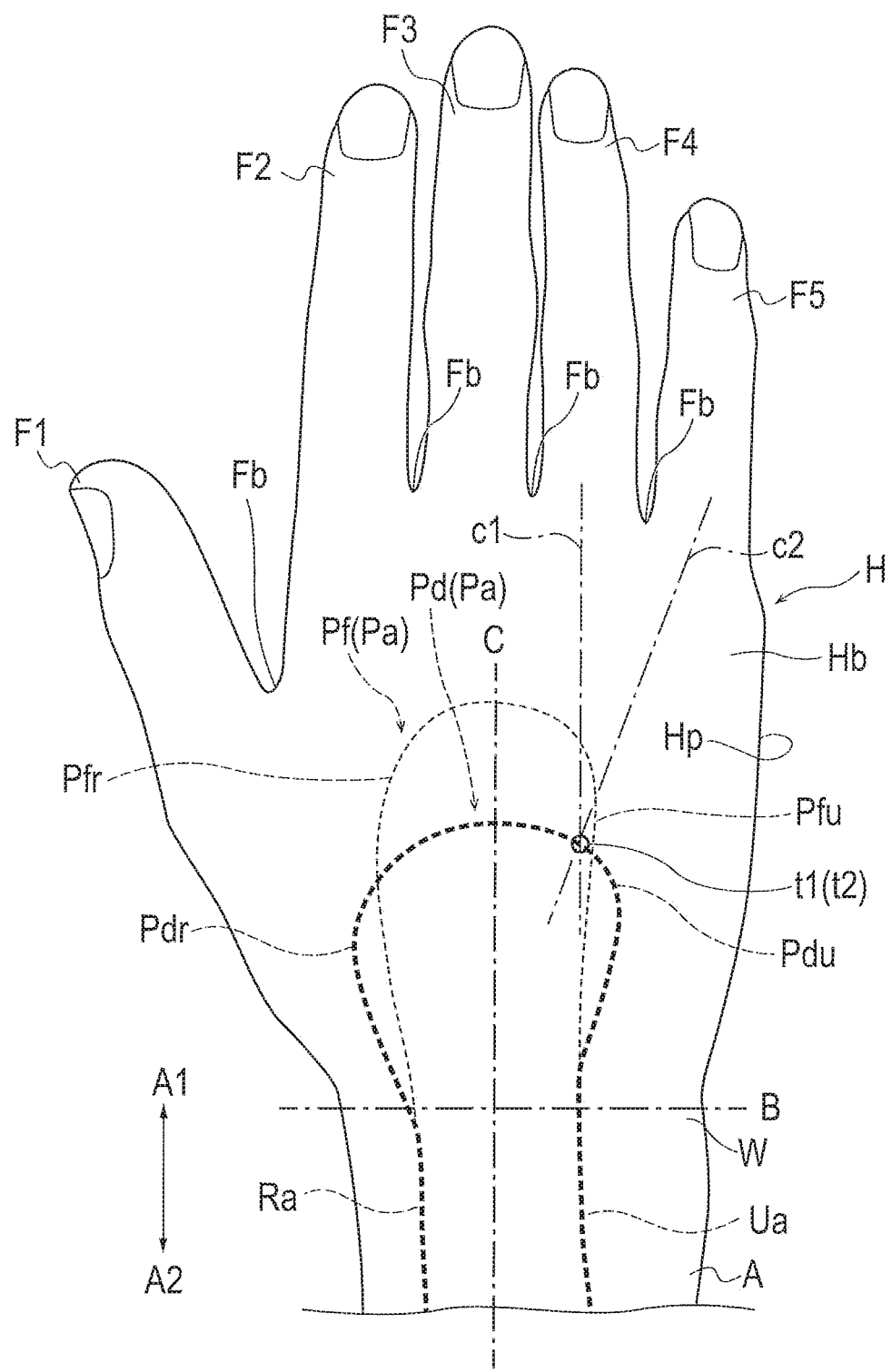
FIG. 6 is a plan view schematically illustrating a structure of the hand of the patient.

As illustrated in FIGS. 1 and 5, in accordance with an exemplary embodiment, the covering portion 110 has an indwelling portion 137 which enables the sheath tube 210 of the introducer 200 to indwell the hemostatic target site t1.

As illustrated in FIG. 1, the indwelling portion 137 is formed on an inner surface of the band portion 130. As illustrated in FIG. 5, the indwelling portion 137 forms a groove in which the sheath tube 210 of the introducer 200 can be located. The groove configuring the indwelling portion 137 has a concave curved shape from the inner surface side of the band portion 130 in a thickness direction of the band portion 130. As illustrated in FIG. 1, the indwelling portion 137 is formed so that one end side faces the outer surface of the band portion 130 and the other end side extends to the vicinity of the pressing portion 160.

Note that, a specific shape or a structure of the indwelling portion 137 is not limited to the groove as illustrated in the drawing. For example, the indwelling portion 137 may be a hole portion (opening portion) formed in the vicinity of the pressing portion 160 of the band portion 130.

As illustrated in FIGS. 2, 3A, and 3B, in a state where the band portion 130 is wrapped around the hand H, the restriction portion 150 is fixed to the band portion 130 through the inter-finger portion Fb present between the ring finger F4 and the little finger F5.

The restriction portion 150 is configured to include a flexible band-like member. The material from which the restriction portion 150 is made, for example, can be a material, which is the same material as that of the band portion 130. Note that, similarly to the band portion 130, the restriction portion 150 may be formed to be transparent (including translucent and colored transparent), or may be formed not to be transparent with a predetermined color.

As illustrated in FIGS. 1, 3A, and 3B, the restriction portion 150 has a first end portion 153 fixed to the band portion 130, and a second end portion 154 facing the first end portion 153 and fixed to the band portion 130.

As illustrated in FIG. 1, the restriction portion 150 is fixed to the band portion 130 so as to form an annular shape. For example, the restriction portion 150 is formed so as to have a width smaller than a width of the band portion 130. The width of the band portion 130 represents a dimension in a direction orthogonal to an extending direction (lateral direction in FIG. 1) of the band portion 130. The width of the restriction portion 150 represents a dimension in a direction orthogonal to an extending direction of the restriction portion 150.

For example, the restriction portion 150 can be formed to have the length in the extending direction (length of the annular portion) of 5 mm to 200 mm, and can be formed to have the width of 1 mm to 50 mm. In addition, for example, the band portion 130 can be formed to have the length in the extending direction of 30 mm to 500 mm, and can be formed to have the width of 3 mm to 100 mm.

For example, at least one of the first end portion 153 and the second end portion 154 of the restriction portion 150 may be formed to be attachable to and detachable from (interlockable with) the band portion 130. For example, in a case where the holding portion 140 of the band portion 130 is formed to be long, a configuration can be adopted as follows. The male side (or the female side) of the hook and loop fastener is located in each of the end portions 153 and 154, and the restriction portion 150 can be attachable to and detachable from the holding portion 140 of the band portion 130. Note that, a holding portion (hook and loop fastener or the like) for attaching and detaching the restriction portion 150 to and from the band portion 130 may be separately provided.

In addition, for example, the restriction portion 150 may be configured to be located between fingers other than the ring finger F4 and the little finger F5. In addition, for example, a plurality of the restriction portions 150 can be disposed in one hemostatic device 100. In this case, the restriction portion 150 may be configured to have a plurality of portions located between different fingers after being branched from the restriction portion 150, or may be configured to have a plurality of portions located between different fingers after being branched from the band portion 130. In a case where the restriction portion 150 has the plurality of portions located between the respective fingers, for example, the restriction portion 150 may be provided with the portion which is attachable to and detachable from the band portion 130 and the portion which is not attachable to and detachable from the band portion 130.

In addition, the restriction portion 150 may be provided with a liquid absorbing layer having liquid absorbing property, in a portion (inner surface of the restriction portion 150) located on a surface layer side of the hand H. For example, the liquid absorbing layer can be formed of a gel having liquid absorbing property (water absorbing property), a fibrous member, or a porous member having liquid absorbing property. The liquid absorbing layer absorbs (adsorbs) a body fluid such as blood flowing to the restriction portion 150 side while hemostasis is performed using the hemostatic device 100. Therefore, the operator can save efforts in carrying out work for wiping off the blood, and can shorten a period of time required for treatment using the hemostatic device 100.

As illustrated in FIG. 4, the pressing portion 160 has an inflatable member 161 and an inflatable space 163 into which a fluid (for example, air) can be injected.

As illustrated in FIG. 4, in accordance with an exemplary embodiment, the pressing portion 160 is inflated by injecting the fluid, and applies a compressive force to the hemostatic target site t1 (puncture site t2) of the hand H of the patient.

The inflatable member 161 can be formed of a flexible sheet-like member. A peripheral edge of the inflatable member 161 is welded (or bonded) to the inner surface of the band portion 130. The inflatable member 161 forms the inflatable space 163 into which the fluid can be injected, between the inflatable member 161 and the inner surface of the band portion 130.

The material from which the inflatable member 161 is made is not particularly limited. For example, the material of the inflatable member 161 can be the same material from which the band portion 130 described above is made.

In accordance with an exemplary embodiment, it can be preferable that the inflatable member 161 is substantially transparent. However, the inflatable member 161 is not limited to the transparent member, and may be translucent or colored transparent.

Note that, the pressing portion 160 may be configured to include a bag-shaped member obtained by folding one sheet and bonding or welding edge portions to each other. Alternatively, the pressing portion 160 may be configured to include a balloon-like member having no edge portion.

In addition, an outer shape of the pressing portion 160 is not particularly limited. For example, in a state where the pressing portion 160 is not inflated, in a plan view, the pressing portion 160 may have the outer shape such as a circle, an ellipse, and a polygon.

In addition, as long as the compressive force can be applied to the hemostatic target site t1, for example, the pressing portion 160 can be configured to include a member which does not have a function of inflating in response to the injected fluid. For example, the pressing portion 160 can include a mechanical member in which the amount of pressing the hand H is variable using an external operation such as rotation, a member which presses the hand H so as to apply surface pressure and which is configured to include a resin material such as plastics or a gel, a member including a hydrophilic gel or a wound material (dressing material) to be brought into contact with the hemostatic target site t1, a member containing a gel whose moisture content decreases with the lapse of time so that the compressive force gradually decreases, an elastic material such as a sponge-like substance, an aggregate of fibers such as cotton (padding), metal, a member having a predetermined three-dimensional shape (spherical shape, ellipsoid shape, or triangular pyramid shape), or a member in which all of these are appropriately combined with each other.

As illustrated in FIGS. 1 and 2, in accordance with an exemplary embodiment, the hemostatic device 100 has an injection portion 170 for inflating and deflating the inflatable member 161 of the pressing portion 160.

As illustrated in FIGS. 1 and 4, the injection portion 170 has a flexible tube 171 whose one end is connected to the pressing portion 160 and whose lumen communicates with the inflatable space 163 of the pressing portion 160, a bag 172 located in a distal portion of the tube 171 so as to communicate with the lumen of the tube 171, and a tubular connector 173 having an incorporated check valve (not illustrated) connected to the bag 172.

As illustrated in FIG. 4, one end portion side connected to the pressing portion 160 in the tube 171 penetrates the band portion 130. An interlock member 138 for interlocking the tube 171 is attached to the band portion 130. Note that, the tube 171 may directly interlock with the band portion 130 by means of welding without interposing a member such as the interlock member 138 therebetween.

When the inflatable member 161 of the pressing portion 160 is inflated (expanded), the operator inserts a distal cylindrical portion of a syringe (not illustrated) into the connector 173, opens the check valve, and pushes a plunger of the syringe so as to inject the air inside the syringe into the inflatable space 163 via the injection portion 170. If the inflatable member 161 is inflated by performing this operation, the bag 172 communicating with the inflatable space 163 via the tube 171 expands. The operator confirms the expansion of the bag 172, thereby enabling the operator to view and easily confirm that the inflatable member 161 is pressurized without any leaking air.

The operator injects the air into the inflatable member 161, and thereafter, removes the distal cylindrical portion of the syringe from the connector 173. In addition, the operator can close the bag 172 by using the check valve incorporated in the connector 173, and thus, the air leakage can be prevented.

As illustrated in FIGS. 2 and 4, in the place covering the pressing portion 160, the band portion 130 has the marker portion 136 for aligning the pressing portion 160 with the hemostatic target site t1 so that both of these overlap each other.

As illustrated in FIG. 2, the marker portion 136 can be located at a substantially central position in a plane direction of the pressing portion 160. In addition, as illustrated in FIG. 4, the marker portion 136 is disposed on the inner surface of the band portion 130.

As illustrated in FIG. 2, the marker portion 136 can be formed in a rectangular shape in a plan view. However, the shape of the marker portion 136 is not particularly limited. For example, the shape may be a circle, a triangle, a square, a star shape, or a pentagon shape.

In addition, the material from which the marker portion 136 is made is not particularly limited. For example, the material can include an oily coloring agent such as ink and a resin kneaded with a pigment.

In addition, a color of the marker portion 136 is not particularly limited as long as the color enables the pressing portion 160 to be aligned with the hemostatic target site t1. However, it can be preferable to use a green color. When the green color is used, the operator can easily view the marker portion 136 in the blood or on the skin. Therefore, the pressing portion 160 can be easily aligned with the hemostatic target site t1.

In addition, it can be preferable that the marker portion 136 is translucent or colored transparent. In this manner, even in a state where the marker portion 136 overlaps the hemostatic target site t1, the operator can view the hemostatic target site t1 from the outer surface side of the marker portion 136.

A method of disposing the marker portion 136 in the band portion 130 is not particularly limited. For example, the method may include a method of printing the marker portion 136 on the band portion 130, a method of welding the marker portion 136 to the band portion 130, and a method of applying an adhesive to one surface of the marker portion 136 so as to adhere to the band portion 130.

Note that, the marker portion 136 may be disposed on the outer surface of the band portion 130. In addition, the marker portion 136 may be disposed in the inflatable member 161 of the pressing portion 160. In this case, it can be preferable that the marker portion 136 is disposed on the inner surface side of the inflatable member 161 so as not to come into direct contact with the hemostatic target site t1 (refer to FIG. 4).

Next, referring to FIGS. 7 to 10, a treatment method and a use procedure of the hemostatic device 100 according to the present embodiment will be described.

As illustrated in FIG. 7, the operator inserts the sheath tube 210 of the introducer 200 into the ulnar artery side Pdu of the palmar artery Pa. Specifically, the operator uses a puncture needle (not illustrated) known in the medical field so as to puncture the skin of the dorsal Hb side of the hand of the patient toward the ulnar artery side Pdu of the palmar artery Pa. In this case, for example, it can be preferable that the operator puncture a site on the distal side (ulnar artery Ua side) of the ulnar artery side Pdu of the palmar artery Pa extending between the bone of the ring finger F4 and the bone of the little finger F5.

Note that, as illustrated in FIG. 7, as the introducer 200, it is possible to use a known introducer including the sheath tube 210, a hub portion 220 located in the proximal portion of the sheath tube 210, a liquid injection tube 230 communicating with the lumen of the hub portion 220, and a dilator tube (not illustrated) which can be inserted into and removed from the sheath tube 210.

Next, the operator inserts a guide wire (not illustrated) into the ulnar artery side Pdu of the palmar artery Pa via the lumen of the puncture needle.

Next, the operator removes the puncture needle out of the living body, while the guide wire remains indwelling the ulnar artery side Pdu of the palmar artery Pa.

Next, the operator inserts the dilator tube inserted into the sheath tube 210 into the ulnar artery side Pdu of the palmar artery Pa from the dorsal Hb side of the hand along the guide wire.

Next, as illustrated in FIG. 7, the operator removes the guide wire and the dilator tube from the ulnar artery side Pdu of the palmar artery Pa, while the sheath tube 210 remains indwelling the ulnar artery side Pdu of the palmar artery Pa. Thereafter, the operator inserts a medical device such as a treatment instrument and a diagnostic instrument, and a guide wire, which delivers these medical devices to the blood vessel having a treatment target lesion site, into the ulnar artery side Pdu of the palmar artery Pa via the sheath tube 210.

The operator inserts the medical device and the guide wire so as to reach a predetermined lesion site (for example, a stenosed site of a coronary artery) via the ulnar artery side Pdu of the palmar artery Pa, the ulnar artery Ua, and the brachial artery. The ulnar artery side Pdu of the palmar artery Pa extends in a state of being gently bent compared to the radial artery side Pdr. Accordingly, the operator can rather smoothly deliver the medical device and the guide wire to the lesion site.

The operator removes the medical device and the guide wire via the sheath tube 210 after completely performing treatment on the lesion site. In this case, the operator removes the medical device and the guide wire out of the living body by way of the brachial artery, the ulnar artery Ua, the ulnar artery side Pdu of the palmar artery Pa, and the puncture site t2 in this order.

Next, the operator performs hemostasis by using the hemostatic device 100.

As illustrated in FIG. 8, the operator locates the band portion 130 of the covering portion 110 around the hemostatic target site t1 of the dorsal Hb side of the hand. In this case, the operator locates a portion of the sheath tube 210 pulled out of the living body so as to align with the indwelling portion 137 formed in the band portion 130 (refer to FIG. 5).

The operator locates the pressing portion 160 so as to overlap the puncture site t2 while causing the sheath tube 210 of the introducer 200 to indwell the puncture site t2 (refer to FIG. 4). In this case, the operator locates the marker portion 136 so as to overlap the hemostatic target site t1, while visibly confirming the marker portion 136 formed in the band portion 130. In this manner, the operator can rather easily align the pressing portion 160 with the puncture site t2.

Note that, in a work stage to start mounting the hemostatic device 100 on the hand H, the hemostatic device 100 is prepared in a state where the pressing portion 160 is not inflated.

As illustrated in FIG. 8, the operator locates the restriction portion 150 so that at least a portion of the restriction portion 150 is caught on the inter-finger portion Fb between the ring finger F4 and the little finger F5. In this case, the operator can easily locate the restriction portion 150 in the inter-finger portion Fb by causing the ring finger F4 or the little finger F5 to pass through the annular portion of the restriction portion 150.

Next, as illustrated in FIG. 9, in a state where the band portion 130 is wrapped around the hand H, the operator joins the holding portion 140 (the male side 140a and the female side 140b of the hook and loop fastener), and fixes the band portion 130 to the hand H.

Note that, in a case where at least one of the first end portion 153 and the second end portion 154 of the restriction portion 150 is formed to be attachable to and detachable from (interlockable with) the band portion 130, in a state where the band portion 130 is wrapped around the hand H, the operator may join the holding portion 140, and may fix the band portion 130 to the hand H. Thereafter, the operator may locate the restriction portion 150 so that at least a portion of the restriction portion 150 is caught on the inter-finger portion Fb between the ring finger F4 and the little finger F5. In this manner, when aligning the pressing portion 160 with the puncture site t2, the operator can rather easily perform fine adjustment of the pressing portion 160 with the puncture site t2.

In accordance with an exemplary embodiment, the operator mounts the hemostatic device 100 on the hand H of the patient so that the injection portion 170 faces the downstream side (palm side) of the blood flow in the ulnar artery Ua. In this manner, when operating the injection portion 170, the operator can help prevent an instrument (for example, a blood pressure monitor) located on the upstream side of the blood flow or a worker who carries out work on the upstream side of the blood flow and the injection portion 170 from interfering with each other. Note that, in a case of the ulnar artery Ua, the upstream side of the blood flow means a direction closer to the heart of the blood vessel, and the downstream side of the blood flow means a direction farther away from the heart of the blood vessel.

Next, the operator connects the syringe (not illustrated) to the connector 173 of the injection portion 170, and injects the air into the pressing portion 160. The pressing portion 160 is inflated by injecting the air, and applies the compressive force to the puncture site t2 formed on the ulnar artery side Pdu of the palmar artery Pa (refer to FIG. 4).

As illustrated in FIG. 10, the operator removes the sheath tube 210 of the introducer 200 from the puncture site t2 while maintaining the compressive force of the pressing portion 160 which is applied to the puncture site t2.

After inflating the pressing portion 160 so as to start hemostasis, the operator can appropriately adjust internal pressure of the pressing portion 160 in accordance with the progress of the hemostasis. For example, after the pressing portion 160 is inflated, in a case where the hemostasis of the puncture site t2 is not sufficiently performed, the operator injects the air again into the pressing portion 160. In this manner, the operator can increase the internal pressure of the pressing portion 160. In addition, for example, in a case where the operator wishes to return the internal pressure of the pressing portion 160 to the initial internal pressure obtained by injecting the air into the pressing portion 160, the operator may inject the air as much as the amount of the air discharged from the pressing portion 160.

The patient can move the arm A, the wrist W, and fingertips while the hemostasis is performed using the hemostatic device 100. Therefore, compared to a case where the hemostasis is performed in a state where the compressive force is applied to the puncture site formed in the arm or the wrist, the patient can more freely adopt various body motions, thereby improving quality of life (QOL).

The operator detaches the hemostatic device 100 from the hand H after a predetermined time elapses and the hemostasis is completely performed on the puncture site t2. In this case, for example, after the band portion 130 is unlocked from the holding portion 140, the operator moves the restriction portion 150 from the inter-finger portion Fb between the ring finger F4 and the little finger F5. In this manner, the operator can conveniently detach the hemostatic device 100 from the hand H.

An operation effect of the treatment method according to the present embodiment will be described.

The treatment method according to the present embodiment includes causing the sheath tube 210 of the introducer 200 introduced into the blood vessel via the puncture site t2 formed on the ulnar artery side Pdu of the palmar artery Pa of the patient to indwell the puncture site t2. According to this treatment method, the sheath tube 210 of the introducer 200 is located on the ulnar artery side Pdu of the palmar artery Pa having less bending of the blood vessel. Accordingly, in a state where the sheath tube 210 of the introducer 200 indwells the blood vessel (for example, the palmar artery or a predetermined blood vessel having a lesion site), the operator can suppress kinking from occurring in the sheath tube 210.

In addition, in the treatment method according to the present embodiment, the medical elongated body is the catheter (the sheath tube 210 of the introducer 200). Then, the treatment method includes introducing the medical device to the palmar artery Pa via the catheter indwelling the puncture site t2, and delivering the medical device to the lesion site in the blood vessel through the ulnar artery side Pdu of the palmar artery Pa.

According to the treatment method described above, the sheath tube 210 of the introducer 200 is located on the ulnar artery side Pdu of the palmar artery Pa having less bent blood vessels. Accordingly, the operator can suppress poor torque transmission ability and poor operability of the medical device introduced into the blood vessel via the sheath tube 210 of the introducer 200.

In addition, the treatment method according to the present embodiment can include removing the medical device from the blood vessel through the ulnar artery Ua and the palmar artery Pa after the treatment is performed on the lesion site using the medical device, locating the hemostatic device 100 around the hemostatic target site t1 present in the hand H of the patient in a state where the sheath tube 210 of the introducer 200 indwells the puncture site t2, and removing the sheath tube 210 of the introducer 200 from the puncture site t2 after the hemostatic device 100 is located.

According to the treatment method described above, the operator performs the hemostasis on the puncture site t2 formed on the ulnar artery side Pdu of the palmar artery Pa of the patient. In this manner, the operator can help prevent motions of the arm A, the wrist W, and the fingertips of the patient from being restricted while the hemostasis is performed. In this manner, the patient can more freely adopt various body motions during the hemostasis, thereby improving quality of life (QOL).

In addition, the hemostatic device 100 includes the covering portion 110 which covers the hemostatic target site t1, and the pressing portion 160 which presses the hemostatic target site t1 in a state where the covering portion 110 covers the hemostatic target site t1. Then, the treatment method includes locating the pressing portion 160 in the hemostatic target site t1 so that the pressing portion 160 overlaps the puncture site t2 while causing the sheath tube 210 of the introducer 200 to indwell the puncture site t2, when the hemostatic device 100 is located around the hemostatic target site t1, fixing the covering portion 110 to the hand H so that the pressing portion 160 presses the puncture site t2, and removing the sheath tube 210 of the introducer 200 from the puncture site t2 while maintaining a state where the pressing portion 160 presses the puncture site t2.

According to the treatment method described above, the operator can help prevent the blood from flowing out of the body when the sheath tube 210 of the introducer 200 is removed from the puncture site t2 formed in the hand H of the patient. Furthermore, after the hemostasis starts, the operator can cause the pressing portion 160 to stably maintain a state where the hemostasis is performed.

In accordance with an exemplary embodiment, the covering portion 110 of the hemostatic device 100 includes the fixing portion 120 which surrounds at least a portion of the hand H while covering the pressing portion 160, and the restriction portion 150 which restricts the movement of the fixing portion 120 in the axial direction. The restriction portion 150 is located between adjacent fingers of the hand H, in a state where the pressing portion 160 fixes the covering portion 110 to the hand H so as to press the puncture site t2.

According to the treatment method described above, in a state where the hand H of the patient is surrounded by the fixing portion 120, the operator can cause the restriction portion 150 located between the adjacent fingers of the hand H to restrict the movement of the hemostatic device 100 in the axial direction (extending direction of the fingers). In this manner, the operator can help prevent a movable range of the fingers of the hand of the patient having the hemostatic device 100 mounted on fingers of the hand from being narrowed (or reduced), or can help prevent the hemostatic device 100 from being misaligned.

In accordance with an exemplary embodiment, the fixing portion 120 of the hemostatic device 100 can include the band portion 130 wrapped around the hemostatic target site t1 of the hand H, and the holding portion 140 which fixes the band portion 130 in a state where the band portion 130 is wrapped around the hand H. In a state where the band portion 130 is wrapped around the hand H, the restriction portion 150 is fixed to the band portion 130 through a portion between the ring finger F4 of the hand H and the little finger F5 of the hand H.

According to the treatment method described above, the operator can cause the holding portion 140 to stably maintain a state where the band portion 130 is wrapped around the hand H. In addition, the operator can help prevent the hemostatic device 100 from being misaligned by using the restriction portion 150 located so as to pass through the inter-finger portion Fb between the ring finger F4 and the little finger F5.

In addition, the catheter is inserted into the ulnar artery side Pdu of the palmar artery Pa from the dorsal Hb side of the hand of the patient, and the hemostatic device 100 is located around the hemostatic target site t1 present on the dorsal Hb side of the hand of the patient. According to the treatment method, the operator punctures the hole, and introduces the sheath tube 210 from the dorsal Hb side of the hand where a muscular layer and a fat layer are relatively thin. Accordingly, the operator can rather smoothly carry out the work.

Next, a treatment method and a hemostatic device 300 according to a second embodiment of the present disclosure will be described. Note that, configurations and members which are not particularly described, or treatment procedures not particularly described in the second embodiment can be regarded as the same as those in the first embodiment described above, and description of the first embodiment will be omitted.

Figure 11:
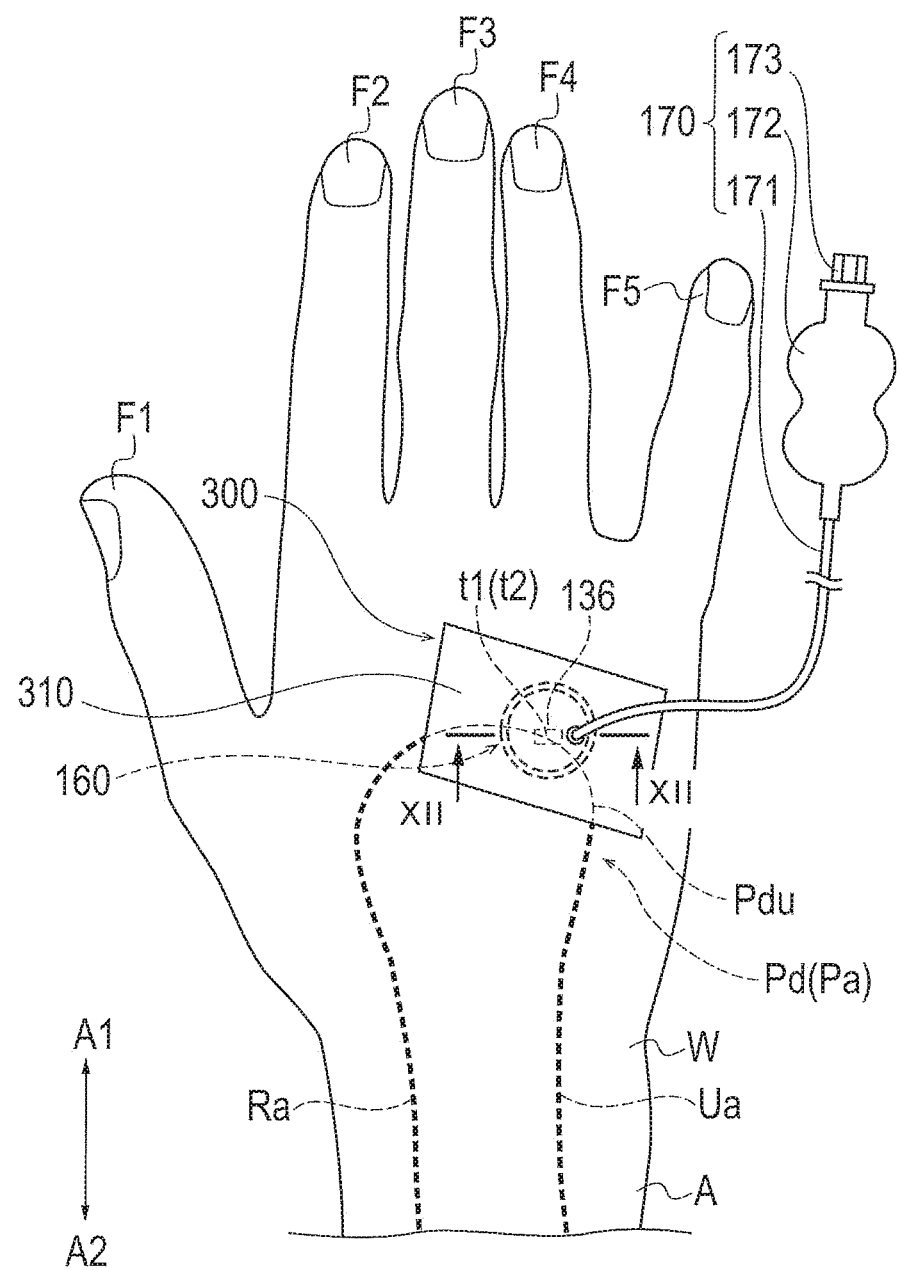
FIG. 11 is a plan view illustrating a state where a hemostatic device according to a second embodiment of the present disclosure is mounted on a hand of a patient.
Figure 12:
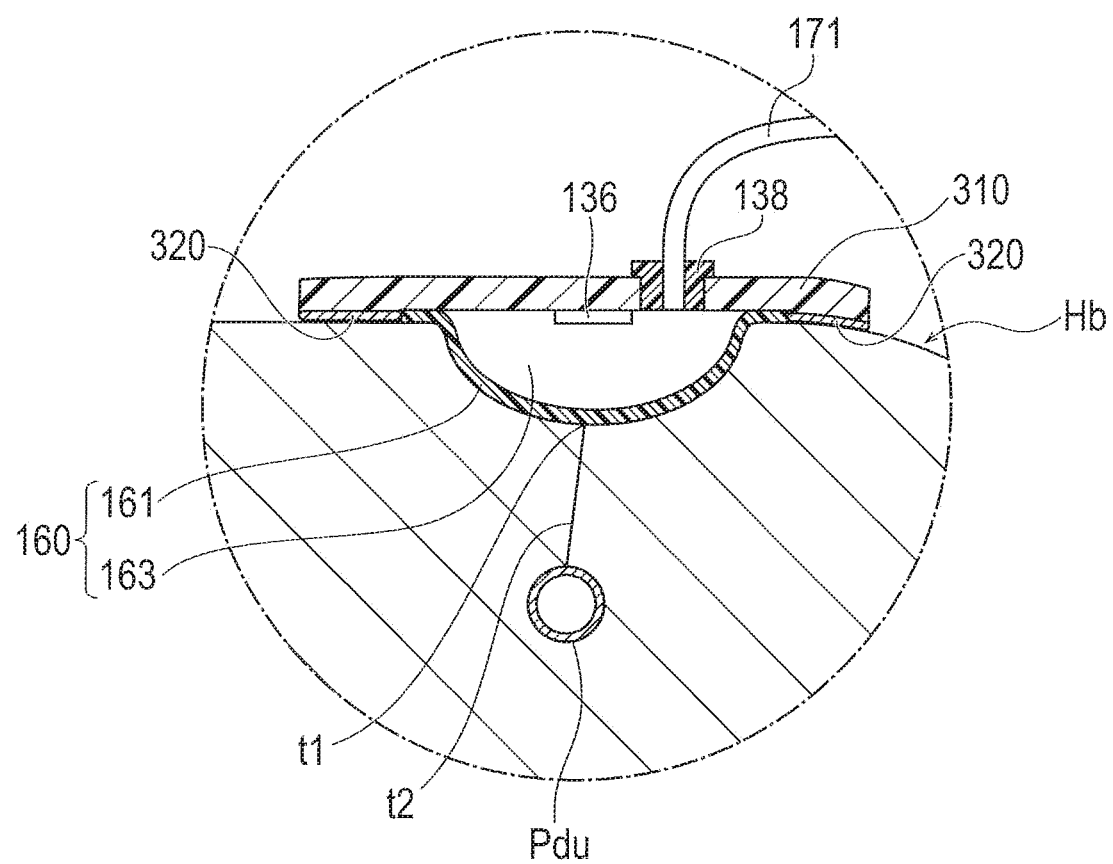
FIG. 12 is an enlarged view illustrating a portion of a cross section taken along line XII-XII illustrated in FIG. 11.

FIG. 11 is a plan view illustrating a state where the hemostatic device 300 according to the second embodiment is mounted on the hand H of the patient, and FIG. 12 is an enlarged cross-sectional view of a portion taken along line XII-XII illustrated in FIG. 11.

The hemostatic device 300 according to the second embodiment differs from the hemostatic device 100 according to the first embodiment in a configuration of a covering portion 310.

As illustrated in FIGS. 11 and 12, the hemostatic device 300 includes the covering portion 310 located so as to cover the hemostatic target site t1 of the hand H of the patient, and the pressing portion 160 which presses the hemostatic target site t1 while the covering portion 310 covers the hemostatic target site t1.

As illustrated in FIG. 12, the covering portion 310 is formed of a sheet-like member, which covers the hemostatic target site t1. The pressing portion 160 is disposed on the inner surface of the covering portion 310. The pressing portion 160 can be welded (or bonded) to the inner surface of the covering portion 310. Note that, the pressing portion 160 can be formed in substantially the same manner as that of the hemostatic device 100 according to the first embodiment.

In accordance with an exemplary embodiment, an adhesive layer 320 is disposed on the inner surface of the covering portion 310 so as to surround the pressing portion 160. For example, it can be preferable that the adhesive layer 320 has a relatively strong fixing force (adhesive force) so that the covering portion 310 can stably maintain a state where the covering portion 310 adheres to the hand H of the patient.

As illustrated in FIGS. 11 and 12, the marker portion 136 can be disposed on the inner surface of the covering portion 310. Note that, the marker portion 136 can be formed in substantially the same manner as that of the hemostatic device 100 according to the first embodiment.

For example, a liquid absorbing layer which can absorb a body fluid such as blood can be disposed around the pressing portion 160 on the inner surface of the covering portion 310.

The hemostatic device 300 may be provided with a protective member (protective sheet) located so as to cover the adhesive layer 320 in a state where the hemostatic device 300 is not used. In a case where the hemostatic device 300 is configured in this way, the operator detaches the protective member from the adhesive layer 320 when using the hemostatic device 300. In this manner, the operator can fix the covering portion 310 to the hand H of the patient.

Next, a use procedure of the hemostatic device 300 according to the second embodiment will be described.

While the sheath tube 210 of the introducer 200 remains indwelling the ulnar artery side Pdu of the palmar artery Pa (refer to FIG. 8), the operator locates the covering portion 310 so as to cover the hemostatic target site t1 formed in the dorsal Hb side of the hand of the patient. In this case, the operator causes the adhesive layer 320 of the covering portion 310 to adhere to the dorsal Hb side of the hand of the patient. In this manner, the operator can fix the hemostatic device 300 to the hand H of the patient.

Next, the operator connects a syringe (not illustrated) to the connector 173 of the injection portion 170, and injects the air into the pressing portion 160. The pressing portion 160 is inflated by injecting the air, and applies the compressive force to the puncture site t2 formed on the ulnar artery side Pdu of the palmar artery Pa (refer to FIG. 12).

While maintaining the compressive force of the pressing portion 160 applied to the puncture site t2, the operator removes the sheath tube 210 of the introducer 200 from the puncture site t2.

The hemostatic device 300 has a relatively simple structure fixed by the adhesive layer 320 in a state where the covering portion 310 covers the hemostatic target site t1. In accordance with an exemplary embodiment, the hemostatic device 300 is not provided with the restriction portion or the fixing portion located in the portion between the adjacent fingers, thereby facilitating work for mounting the hemostatic device 300 on the hand H of the patient. Furthermore, the hemostatic device 300 does not restrict the movement of the fingers of the patient in a state where the hemostatic device 300 is mounted on the hand H of the patient.

After a predetermined time elapses and the hemostasis is completely performed on the puncture site t2, the operator detaches the hemostatic device 300 from the dorsal Hb side of the hand of the patient. In this case, the operator can detach the hemostatic device 300 by pulling the covering portion 310 away from the dorsal Hb side of the hand of the patient.

As described above, according to the treatment method in the second embodiment, in a state where the covering portion 310 covers the hemostatic target site t1 of the hand H of the patient, the operator can cause the pressing portion 160 to apply the compressive force to the hemostatic target site t1. Therefore, the patient can more freely adopt various body motions of the arm A, the wrist W, and the fingers F1 to F5 while the hemostasis is performed, thereby improving quality of life (QOL).

Next, a treatment method and a hemostatic device 400 according to a third embodiment of the present disclosure will be described. Note that, configurations and members which are not particularly described, or treatment procedures not particularly described in the third embodiment can be regarded as the same as those in the first embodiment described above, and description of the first embodiment will be omitted.

Figure 13:
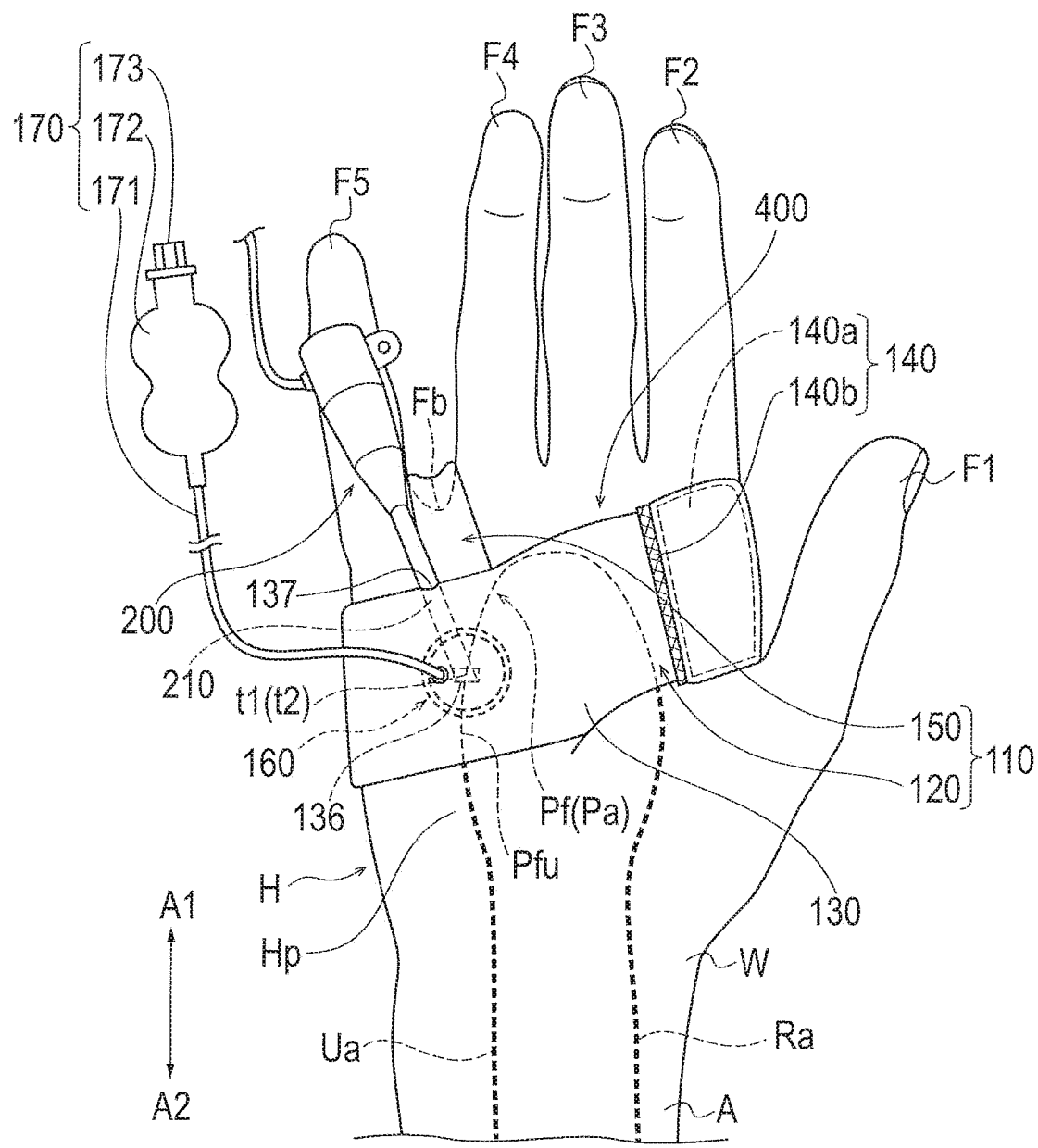
FIG. 13 is a plan view illustrating a state where a hemostatic device according to a third embodiment of the present disclosure is mounted on a hand of a patient.

FIG. 13 is a plan view illustrating a state where the hemostatic device 400 according to the third embodiment is mounted on the hand H of the patient. Note that, FIG. 13 illustrates a state where the hemostatic device 400 is mounted on the hand H of the patient in a state where the sheath tube 210 of the introducer 200 indwells the hand H of the patient.

As illustrated in FIG. 13, in the treatment method according to the third embodiment, the operator forms the puncture site t2 on the palm Hp side of the patient. More specifically, the operator forms the puncture site t2 in the ulnar artery side Pfu of the superficial palmar artery Pf which extends to the ulnar artery Ua side within the superficial palmar artery Pf included in the palmar artery Pa.

The superficial palmar artery Pf extends closer to the palm Hp side than the dorsal Hb side of the hand. Therefore, the operator can cause the puncture needle to rather easily puncture the ulnar artery side Pfu of the superficial palmar artery Pf. In addition, the palm Hp side has fewer bones which are obstructive to the puncture, compared to the dorsal Hb side of the hand. Accordingly, the operator can cause the puncture needle to rather easily puncture the ulnar artery side Pfu of the superficial palmar artery Pf. However, the palm Hp side has a thicker muscle layer and a thicker fat layer, compared to the dorsal Hb side of the hand. Accordingly, in order to enable the puncture site t2 to be formed at a desired position, for example, it can be preferable that the operator performs an echo guide, which can be used to safely insert the puncture needle into the desired position (or vessel).

In accordance with an exemplary embodiment, as illustrated in FIG. 13, for example, it can be preferable to form the puncture site t2 between the little finger F5 and the ring finger F4, rather than between the middle finger F3 and the ring finger F4. When the operator forms the puncture site t2 between the little finger F5 and the ring finger F4, the operator can locate the sheath tube 210 of the introducer 200 so as to be relatively straight along the ulnar artery side Pfu of the superficial palmar artery Pf.

Note that, for example, the hemostatic device 400 has a basic structure which is the same as that of the above-described hemostatic device 100. Moreover, as illustrated in FIG. 13, it is possible to appropriately change a positional relationship between respective portions of the device so that the restriction portion 150 is located in the inter-finger portion Fb between the little finger F5 and the ring finger F4 in a state where the pressing portion 160 is located on the palm Hp side.

Even in a case where the puncture site t2 is formed on the ulnar artery side Pfu of the superficial palmar artery Pf as in the present embodiment, according to this treatment method, the sheath tube 210 of the introducer 200 is located on the ulnar artery side Pdu of the palmar artery Pa having relatively less bending of the blood vessel. Accordingly, in a state where the sheath tube 210 of the introducer 200 indwells the blood vessel, the operator can suppress kinking from occurring in the sheath tube 210. In addition, the patient can more freely adopt various body motions of the arm A, the wrist W, and the fingertips while the hemostasis is performed, thereby improving quality of life (QOL).

Hitherto, the hemostatic device according to the present disclosure has been described with reference to a plurality of the embodiments. However, the present disclosure is not limited only to the respective configurations described above, and can be appropriately modified, based on the description in appended claims.

For example, the treatment method described with reference to the respective embodiments is not particularly limited to a specific hemostatic position (position to which the compressive force is applied) as long as the treatment aims to perform the hemostasis on the puncture site formed on the ulnar artery side of the palmar artery in the hand.

In addition, the hand on which the hemostasis is performed using the above-described treatment method may be any hand between the right and left hands of the patient.

In addition, for example, the operator may puncture the ulnar artery side of the deep palmar artery from the palm side, or may puncture the ulnar artery side of the superficial palmar artery from the dorsal side of the hand.

In addition, in the respective embodiments, the sheath tube (catheter) of the introducer has been described as an example of the medical elongated body inserted into the palmar artery via the puncture site. However, a specific type of the medical elongated body is not particularly limited. For example, the medical elongated body may be a guide wire or a guiding sheath.

In addition, in the respective embodiments, the band portion is located between the thumb and the index finger in a state where the band portion is wrapped around the hand. However, the position of the band portion in a state where the band portion is wrapped around the hand is not particularly limited. For example, the band portion may be located at a position closer to the wrist side than the root of the thumb in a state where the band portion is wrapped around the hand.

In addition, the hemostatic device described in the respective embodiments and modification examples is merely an example. Each portion constituting the hemostatic device can be replaced with any desired configuration (member) which can fulfill the same function. In addition, the hemostatic device may be appropriately provided with any desired additional configuration (member) which is not particularly described herein.

The detailed description above describes a treatment method of introducing a medical elongated body into a palmar artery of a patient. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
   a covering portion configured to be disposed to cover a site where bleeding is to be stopped on a hand of a patient, the covering portion including an elongated band and a restriction portion;
   a pressing portion configured to compress the site where bleeding is to be stopped when the covering portion covers the site where bleeding is to be stopped;
   the elongated band configured to be wrapped around a periphery of the patient's hand at the site where bleeding is to stopped, the pressing portion being mounted on the elongated band at a position between free ends of the elongated band, the elongated band extending from the position between the free ends of the elongated band in a first axial direction towards one of the free ends of the elongated band and from the position between the free ends of the elongated band in a second axial direction towards an other of the free ends of the elongated band, the pressing portion being located closer to the one of the free ends of the elongated band than the other of the free ends of the elongated band, the elongated band including a securing portion that secures the elongated band in a state in which the elongated band is configured to be wrapped around the periphery of the hand of the patient at the site where bleeding is to be stopped, wherein a width of the elongated band is uniform extending between the free ends of the elongated band;
   the restriction portion configured to restrict movement of the securing portion in an axial direction, the restriction portion including a first end portion secured to the elongated band, a second end portion that is attachable to and detachable from the elongated band and an intermediate portion located between the first end portion and the second end portion, the restriction portion configured to be positioned between adjacent fingers of the hand of the patient and possessing a centerline extending parallel to an extending direction of the intermediate portion and extending through a center of a width of the intermediate portion; and
   wherein the pressing portion is not disposed on the centerline of the restriction portion.

2. The hemostatic device according to claim 1, wherein the pressing portion includes a center portion located at a center position in a plane direction of the pressing portion, the center portion of the pressing portion is not disposed on the centerline of the restriction portion.

3. The hemostatic device according to claim 1, further comprising:
   a marker portion for aligning the pressing portion with the site where bleeding is to be stopped so that the pressing portion is configured to overlie the site where bleeding is to be stopped.

4. The hemostatic device according to claim 3, wherein the marker portion is not disposed on the centerline of the restriction portion.

5. The hemostatic device according to claim 3, wherein the marker portion and the pressing portion are positioned in overlying relation to one another.

6. The hemostatic device according to claim 1, wherein the centerline of the restriction portion is orthogonal to the elongated band.

7. The hemostatic device according to claim 1, wherein the restriction portion is configured so that when the second end portion of the restriction portion is attached with the elongated band, the intermediate portion of the restriction portion located between the first end portion and the second end portion of the restriction portion is configured to pass the two adjacent fingers; and
   wherein the two adjacent fingers is a ring finger and a little finger of the hand of the patient.

8. The hemostatic device according to claim 1, wherein the covering portion includes a through opening that passes through the covering portion to enable a medical elongated body to pass through the through opening and indwell at the site where bleeding is to be stopped.

9. The hemostatic device according to claim 1, wherein the pressing portion is inflatable and includes an interior into which fluid is introduced to expand the pressing portion.

10. The hemostatic device according to claim 1, wherein the restriction portion includes a liquid absorbing layer that possesses a liquid absorbing property to absorb liquid on an inner surface of the restriction portion, the liquid absorbing layer being positioned on a side of the restriction portion that is configured to face the hand of the patient when the restriction portion is configured to be positioned between the adjacent fingers.

11. The hemostatic device according to claim 1, wherein the restriction portion forms an annular shape when attached to the elongated band.

12. The hemostatic device according to claim 1, wherein the restriction portion has a width that is less than the width of the elongated band.

13. A hemostatic device comprising:
   a covering portion configured to cover a site where bleeding is to be stopped on a hand of a patient, the covering portion including an elongated band and a restriction portion;
   a pressing portion configured to compress the site where bleeding is to be stopped when the covering portion covers the site where bleeding is to be stopped;
   the elongated band configured to be wrapped around a periphery of the patient's hand at the site where bleeding is to stopped, the pressing portion being mounted on the elongated band at a position between free ends of the elongated band, the elongated band extending from the position between the free ends of the elongated band in a first axial direction towards one of the free ends of the elongated band and from the position between the free ends of the elongated band in a second axial direction towards an other of the free ends of the elongated band, the pressing portion being located closer to the one of the free ends of the elongated band than the other of the free ends of the elongated band, the elongated band including a securing portion that secures the elongated band in a state in which the elongated band is configured to be wrapped around the periphery of the hand of the patient at the site where bleeding is to be stopped, wherein a width of the elongated band is uniform extending between the free ends of the elongated band;

the restriction portion configured to restrict movement of the securing portion in an axial direction, the restriction portion including a first end portion secured to the elongated band and a second end portion that is attachable to and detachable from the elongated band, the restriction portion being positionable between adjacent fingers of the hand of the patient; and the hemostatic device being configured so that in a state in which the second end portion of the restriction portion is attached with the elongated band while the elongated band is wrapped around the periphery of the patient's hand at the site where the bleeding is to be stopped, the pressing portion is not disposed on a centerline of the restriction portion extending from the first end portion secured to the elongated band towards a position of the restriction portion between the adjacent fingers of the hand of the patient.

14. The hemostatic device according to claim 13, further comprising:
a marker portion for aligning the pressing portion with the site where bleeding is to be stopped so that the pressing portion is configured to overlie the site where bleeding is to be stopped; and
wherein the marker portion is not disposed on the centerline of the restriction portion.

15. The hemostatic device according to claim 13, wherein the centerline of the restriction portion is orthogonal to the elongated part band.

16. A hemostatic device comprising:
a covering portion configured to cover a site where bleeding is to be stopped on a hand of a patient;
an expandable pressing portion configured to be expandable and to apply a compressive force to the site where bleeding is to be stopped when the covering portion covers the site where bleeding is to be stopped, the expandable pressing portion possessing a center portion located at a center position in a plane direction of the expandable pressing portion;
the covering portion including:
an elongated band, the elongated band including a first band part and a second band part, the first band part extends away from the expandable pressing portion in a first axial direction, the first band part including one end fixed relative to the expandable pressing portion and an opposite free end, the first band part including a first fastener, the free end of the first band part being spaced from a center of the expandable pressing portion by a first distance, and the second band part extends away from the expandable pressing portion in a second axial direction, the second band part including one end fixed relative to the expandable pressing portion and an opposite free end, the second band part including a second fastener, the free end of the second band part being spaced from the center of the expandable pressing portion by a second distance, the second distance being greater than the first distance, wherein a width of the elongated band is uniform between the free end of the first band part and the free end of the second band part;

the first band part and the second band part possessing respective lengths configured to allow the first band part and the second band part to be wrapped around a periphery of the patient's hand while the expandable pressing portion is configured to overlie the site where bleeding is to be stopped and to allow the first and second fasteners to detachably engage one another to hold the expandable pressing portion on the patient's hand at the site where bleeding is to be stopped;

a third band part including one end fixed relative to the expandable pressing portion and an opposite free end, the third band part extending in a third axial direction different from the first and second axial directions, the third band part including a third fastener, the third band part also including an intermediate portion located between the one end and the opposite free end of the third band, the third band part possessing a centerline extending parallel to the third direction and extending through a center of a width of the intermediate portion;

the third band part possessing a length allowing the intermediate portion of the third band part to be positioned between two fingers of the hand of the patient and allowing the third fastener to be detachably engage the first fastener of the first band part or the second fastener of the second band part to restrict movement of the expandable pressing portion in an axial direction; and the centerline of the third band part is offset to the center portion of the expandable pressing portion.

17. The hemostatic device according to claim 16, further comprising:
a visually identifiable marker for aligning the expandable pressing portion with the site where bleeding is to be stopped, the visually identifiable marker and the expandable pressing portion overlying one another so that positioning the visually identifiable marker to overlie the site where bleeding is to be stopped results in the expandable pressing portion being positioned to overlie the site where bleeding is to be stopped.

18. The hemostatic device according to claim 16, wherein a transparent part of the covering portion overlies the expandable pressing portion.

19. The hemostatic device according to claim 16, wherein the expandable pressing portion is inflatable and includes an interior into which fluid is introduced to expand the expandable pressing portion.

20. A hemostatic device comprising:
a covering portion configured to cover a site where bleeding is to be stopped on a hand of a patient, the covering portion including an elongated band and a restriction portion;
a pressing portion configured to compress the site where bleeding is to be stopped when the covering portion covers the site where bleeding is to be stopped, the pressing portion comprising a marker portion for aligning the pressing portion with the site where bleeding is to be stopped so that the pressing portion is configured to overlie the site where bleeding is to be stopped;
the elongated band configured to be wrapped around a periphery of the patient's hand at the site where bleeding is to be stopped, the pressing portion being mounted on the elongated band at a position between free ends of the elongated band, the elongated band extending from the position between the free ends of the elongated band in a first axial direction towards one of the free ends of the elongated band and from the position between the free ends of the elongated band in a second axial direction towards an other of the free ends of the elongated band, the pressing portion being located closer to the one of the free ends of the elongated band than the other of the free ends of the elongated band, the elongated band including a holding portion that secures the elongated band in a state in which the elongated band is configured to be wrapped around the periphery of the hand of the patient at the site where bleeding is to be stopped, wherein a width of the elongated band is uniform extending between the free ends of the elongated band;

the restriction portion configured to restrict movement of the holding portion in an axial direction, the restriction portion including a first end portion secured to the elongated band and a second end portion that is attachable to and detachable from the elongated band, the restriction portion being positionable between adjacent fingers of the hand of the patient; and the hemostatic device being configured so that in a state in which the second end portion of the restriction portion is attached with the elongated band while the elongated band is wrapped around the periphery of the patient's hand at the site where the bleeding is to be stopped, the marker portion is offset on a centerline of the restriction portion extending from the first end portion secured to the elongated band towards a position of the restriction portion between the adjacent fingers of the hand of the patient.

* * * * *